United States Patent [19]

Bayerl et al.

[11] Patent Number: 5,670,631
[45] Date of Patent: Sep. 23, 1997

[54] PROCEDURE OF SEPARATION OF PROTEINS BY COLUMN CHROMATOGRAPHY USING SILICA GELS COATED BY A LIPID BILAYER

[75] Inventors: Thomas Bayerl; Sybille Bayerl, both of Waldstr. 15, D-85757 Karlsfeld, Germany

[73] Assignees: Thomas Bayerl; Sybille Bayerl, both of Karlsfeld, Germany

[21] Appl. No.: 351,172

[22] Filed: Nov. 30, 1994

[51] Int. Cl.$^6$ .............. C07K 1/14; C07K 1/16; C07K 1/18; C07K 1/34
[52] U.S. Cl. .............. 530/412; 530/416; 530/417
[58] Field of Search .............. 530/412–417

[56] References Cited

U.S. PATENT DOCUMENTS 5,310,648  5/1994  Arniold et al. .............. 435/5

OTHER PUBLICATIONS

Chemical Abstract; vol. 113, 147546T, 1990.

*Primary Examiner*—Ponnathapura Achutamurthy
*Attorney, Agent, or Firm*—Antonelli, Terry, Stout & Kraus, LLP.

[57] ABSTRACT

A chromatography column packing material and column chromatographic methods using a silica gel based column packing material are disclosed. The silica gel material is coated by a phospholipid bilayer containing at least two lipids, at least one having an electric charge. Proteins are separated using this column packing material without denaturing because of the lipid coating. The protein molecule binds to the lipid bilayer coated silica gel and is then eluted by raising the temperature.

17 Claims, 3 Drawing Sheets

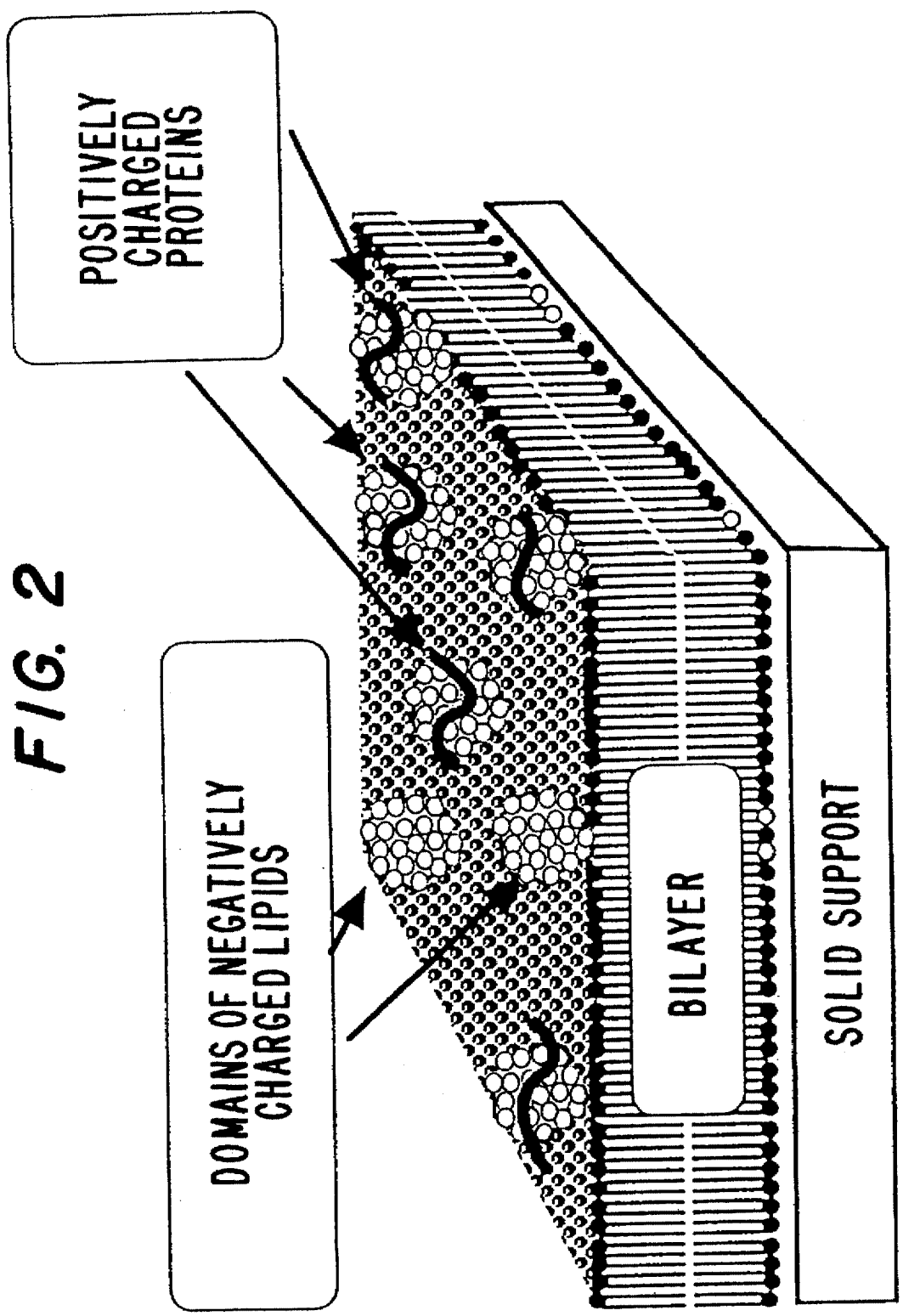

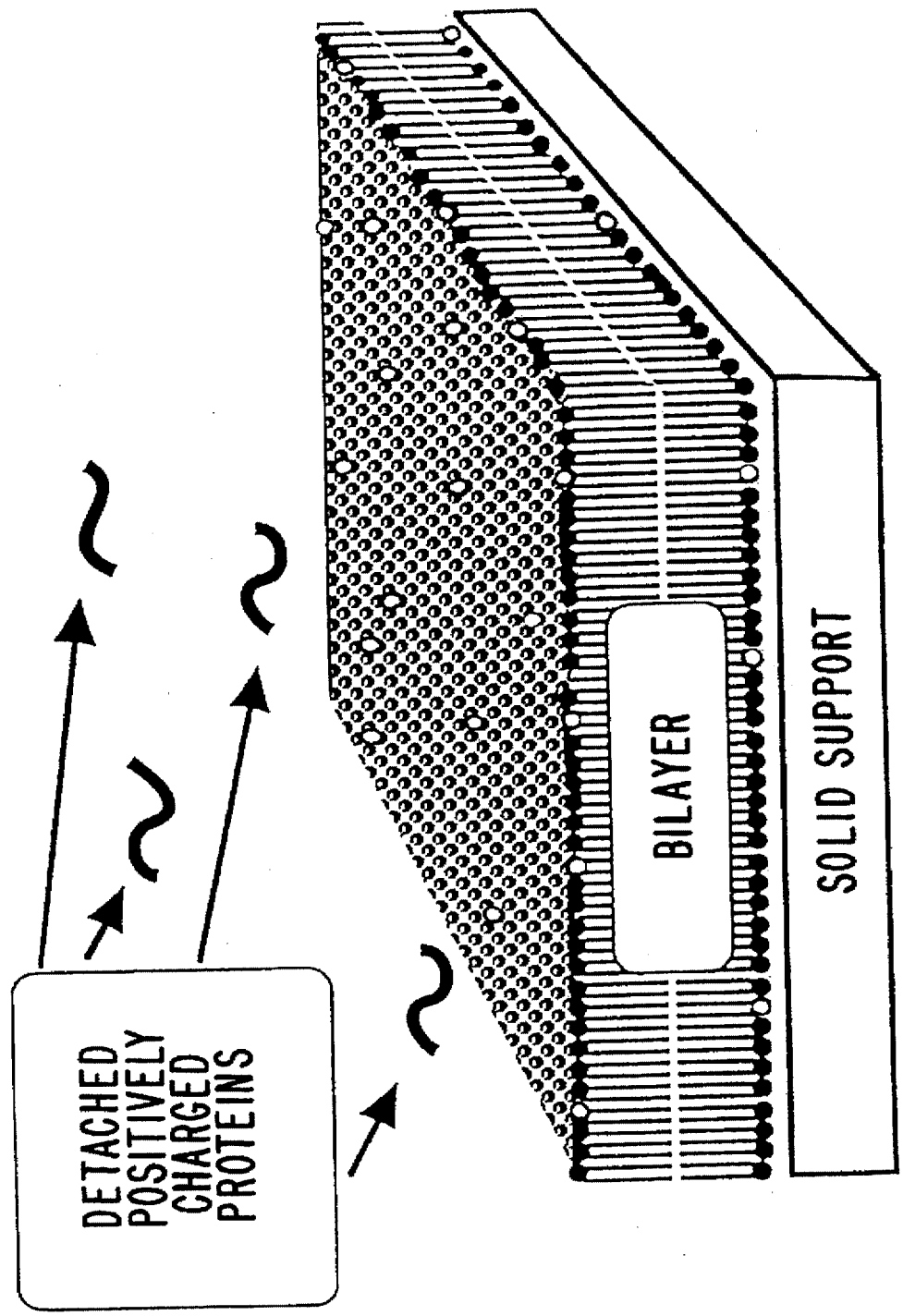

PROCEDURE OF SEPARATION OF PROTEINS BY COLUMN CHROMATOGRAPHY USING SILICA GELS COATED BY A LIPID BILAYER

BACKGROUND OF THE INVENTION (a) Field of the Invention

The present invention relates to a procedure of protein separation and more specifically to a column chromatography method, (b) Description of the Prior Art Column chromatography is a basic procedure in biochemistry for separating proteins and peptides with respect to their size or molecular weight (the so-called gel filtration) or to their electric charge state (ion exchange chromatography).

For gel filtration a chromatography column is filled with a water swelling polymer or with a silica gel (i.e. porous spheres of silicon dioxide) and then the protein mixture to be separated (dissolved in buffer) is layered on top of the gel bed in the column. After this, the column top is supplied with a continous inflow of buffer which causes a flux of the protein mixture through the gel towards the column exit. On passing through the column smaller proteins of the mixture get retarded compared to the larger ones owing to the higher interaction strength of the former with the gel. Thus, a fraction collector connected to the column exit enables the sequential collection of protein fractions ordered by their size. This procedure is described in chapter 5, pp. 157 of B. Cooper's book with the title "Biochemische Arbeitsmethoden" (in German), de Gruyter Publishers, Berlin, N.Y. 1981.

Ion exchange chromatography uses the same basic principle as gel filtration. However, in this case the chromatography gels feature electrically charged groups which are covalently bound to their surface. These gels bind proteins with the corresponding opposite charge state while allowing other proteins which are electrically neutral or of the same charge state as the gel surface to pass the gel freely or may even accelerate their passage due to electrostatic repulsion. After the non-bound proteins have left the column, it is flushed with a buffer solution containing a high concentration of ions with an opposite charge to the gel surface. As a result, the ions replace the proteins at the gel binding sites and the detached proteins can be eluted at the column exit. In some cases surfactant solutions are used for detaching the proteins. The procedure results in protein fractions of different charge states as discussed in chapter 4, pp. 126 of B. Cooper's book with the title "Biochemische Arbeitsmethoden" (in german), de Gruyter Publishers, Berlin, N.Y. 1981.

Denaturation of the protein during the procedure can be a problem with both of the above chromatographic methods. This may be caused by contacts between the protein and inorganic surfaces inside the column and may cause significant reductions of protein activity when silica gels are used. To overcome this problem, silica gels are available which have been treated with organic (e.g. polymeric) coatings. The aim of this treatment is to provide surface properties which the protein "feels" as natural, a so-called biocompatible surface. Examples are latex gels with dextran molecules bound to their surface or silica gels with a covalently bound monolayer of phospholipids (a major component of biological membranes), which leads to an immobilized membrane. These treatments require significant technical efforts which makes the gels rather expensive.

There is another problem with ion exchange chromatography. The detachment of the electrostatically bound proteins by the ions from the gel surface can cause denaturation of the protein. An object of the invention is to reduce significantly the technical requirements for the biocompatibilization of silica gels and to offer new options for the detachment of the proteins from the gel without the risk of protein denaturation.

SUMMARY OF THE INVENTION

The primary object of the present invention is to provide a procedure that enables the chromatographic separation of proteins from a mixture according to their electric charge state using a chromatography gel that enables the charge selective coupling and uncoupling of proteins to its surface without causing significant denaturation of these proteins in the course of the separation process.

Another object of the present invention is to provide a procedure for the biocompatibilization of inorganic silica surfaces that is significantly simpler and less expensive to accomplish while giving biocompatible surfaces of the highest standard. According to the present invention, these objects can be accomplished by coating a silica gel (i.e. porous spheres of silicon dioxide) with a lipid bilayer consisting of at least two lipid components. One of the lipids carries an electric headgroup charge and the other one is electrically neutral at a given pH value of the buffer medium which surrounds the gel. Moreover, the mixing behavior of the two lipids is non-ideal and exhibits a miscibility gap. Then the charge selective coupling of a protein which is dissolved in the surrounding buffer medium to the coated silica gel surface can be accomplished by keeping the temperature of the gel below a certain critical temperature region (the so-called coexistence region) over which the lipid mixture undergoes a transition from a low temperature crystalline phase to a high temperature fluid phase. The miscibility gap of the lipid mixture ensures that at temperatures below the critical region lipid domains of sufficiently high surface charge density are formed that proteins with the opposite charge state can couple to it via coulomb interaction. On the other side, proteins with the same charge state as the domains undergo a repulsion upon approaching the gel surface and neutral proteins remain unaffected. By means of this principle, proteins of a certain charge state (either positive or negative in sign) can be isolated from the bulk proteins. To collect the isolated proteins, the temperature of the gel is raised above that of the coexistence region. This causes the lipid domains to disappear due to the onset of lateral diffusion of the lipid molecules in the plane of the bilayer. As a result, the lipid component carrying the charged headgroup is now homogeneously distributed over the gel surface and the remaining (local) surface charge is insufficient to keep the protein coupled to the surface. The protein detaches and can be collected. The denaturation of the protein in the course of the process is largely prevented by the following reasons. The coupling to the silica gel surface is soft and the surface itself is biocompatible since it represents the surface of a simple biological membrane.

This biocompatibilization of a surface by coating it with a lipid bilayer can generally overcome the problem of denaturation of proteins during a simple gel chromatograpy. To accomplish this, the present invention suggests the coating of the chromatography gel with single component bilayer consisting of an electrically neutral phospholipid at a given pH value of the surrounding buffer medium.

BRIEF DESCRIPTION OF THE DRAWINGS

FIG. 2: Schematic drawing of a bilayer coated to a solid surface where the bilayer consists of a binary lipid mixture that exhibits at a certain temperature domains of high surface charge density to which proteins from the bulk can couple via Coulomb interaction.

FIG. 3: Schematic drawing representing the situation from FIG. 2 after raising the temperature above the phase transition temperature.

DESCRIPTION OF THE PREFERRED EMBODIMENTS

Figure 1:
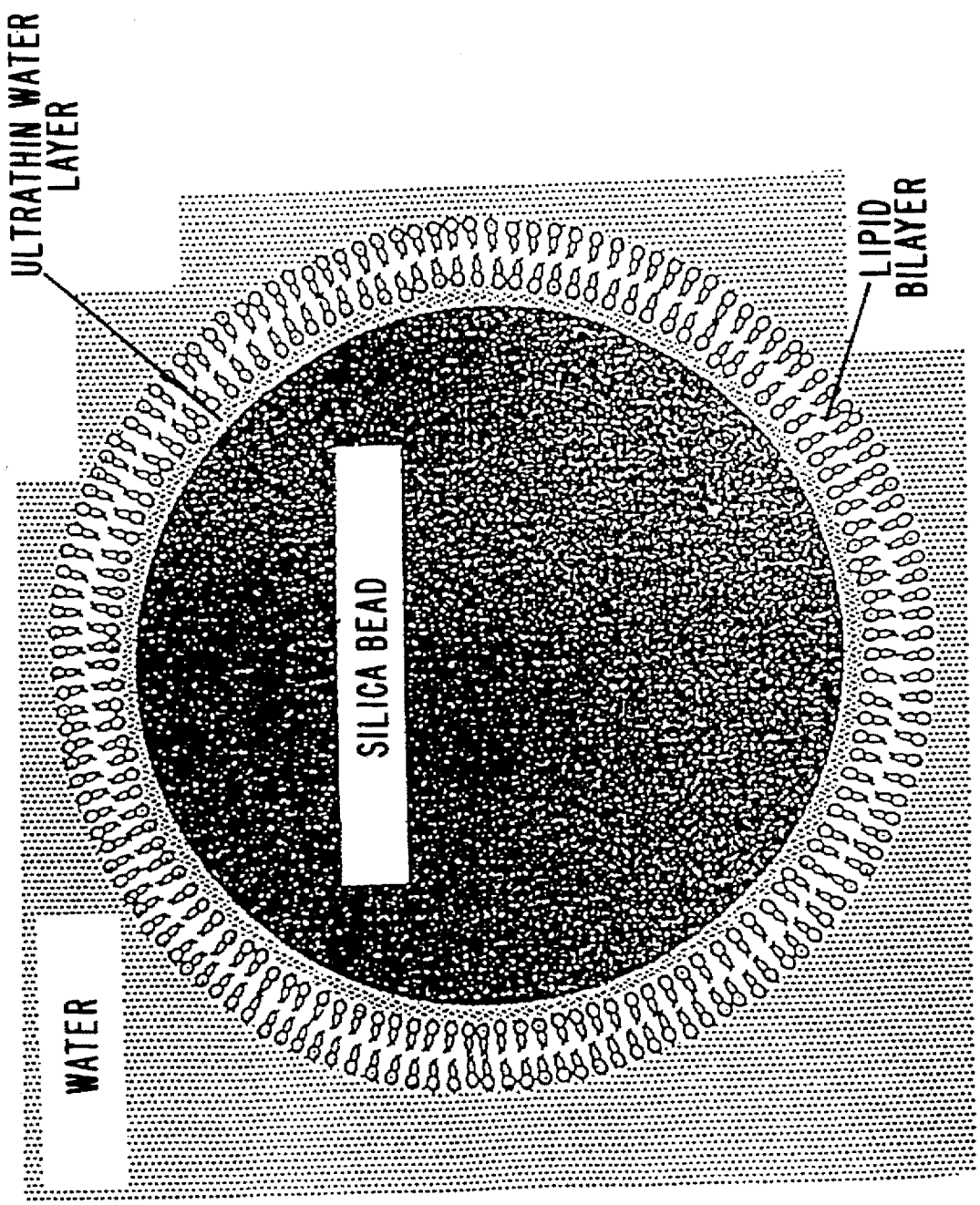
FIG. 1: Schematic drawing of a bilayer coated silica bead. Note the existence of an ultrathin water layer between the silica surface and the bilayer.

The invention is based on well established column chromatography methods (i.e. gel chromatography, ion exchange chromatography). Spherical particles of glass or silica with colloid dimensions (nm–µm range) are packed in a standard chromatography column. In contrast to the above mentioned methods, the spherical particles are coated with a single lipid bilayer with a thickness of about 50–60 Å. FIG. 1 shows schematically that a water layer of 10–20 Å thickness exists between the bilayer and the solid surface. The lipid composition of the bilayer can be either natural lipid species extracted from tissue or of synthetic origin. The preparation method for the coating has been published by T. M. Bayerl (inventor of the present patent application) and M. Bloom in "Physical properties of single phospholipid bilayers adsorbed to micro glass beads", Biophysical Journal 58: 357–362, 1990. There it was shown that such bilayer coated spheres are stable over weeks and that the bilayer itself withstands mechanical and hydrodynamic forces like those exerted on the bilayer by a flow field or during centrifugation of the beads.

The advantages of using bilayer coated silica gels for the purpose of column chromatography can be summarized as follows:

i) The complete screening of the silica surface from the proteins by the lipid bilayer prevents any direct contacts between them. Instead the proteins can now interact with the bilayer surface which may prevent their denaturation. Lipids as constituents of any membrane are truly biological amphiphilics and lipid bilayers exhibit an extreme softness. These features may prevent any protein denaturation. Thus, the bead is coated with a biocompatible surface. This can improve the yield in protein activity of a chromatographic run and may enable the separation of very delicate proteins, which are currently considered as hard to separate (cf. embodiment 1, below).

ii) A further advantage of the invention is the possible use of electrostatic surface charge effects for a charge selective protein separation. Though lecithin (phosphatidylcholine), the major phospholipid component of eucaryotic cells is electrically neutral over a wide pH range, there exists a variety of other phospholipids which possess a negative excess charge (e.g. phosphatidylserine, phosphatidylglycerol, cardiolipin). Thus, by an admixture of such lipids in the coating used for the silica gels a well defined negative surface charge of the bilayer surrounding the bead can be established. This causes proteins with electrically positive charge states to be retarded or even coupled to the bilayer surface via attractive Coulomb interaction without significant denaturation while negatively charged proteins get accelerated on their way through the column. Even positively charged bilayer surfaces can be prepared by using positively charged, lipid-like amphiphiles if the separation task requires it. Hence, the invention enables a sort of ion exchange chromatography (cf. example 2, below).

iii) A further important advantage of the present invention lies in the use of a lipid bilayer instead of, e.g., an immobilized membrane (a lipid monolayer covalently bound to the silica surface). The preparation method (cf. example 1, below) enables the coating of the beads right in the chromatography column prior to the addition of the protein mixture to be separated. The procedure is versatile and inexpensive since it requires only the packing of beads of desired size (which can be stored over years) into the column and the coating with the bilayer. Even modifications of the lipid composition of the bilayer surrounding the beads (and thus of the bilayer surface charge) can be accomplished without removing the beads from the column. This shows the superiority of the present invention over the immobilized membranes, whose preparation is much more complex and cannot be done when packed in a column.

iv) Finally, such lipid bilayer coated silica can be used for the charge selective separation of proteins by employing the mixing properties of binary lipid mixtures. Pure synthetic lipids (i.e. those with saturated fatty acids) exhibit a sharp and reversible first order phase transition between a crystalline and a fluid-crystalline state as discussed by E. Sackmann in "Polymorphism in lipid/water systems" on p. 425 in Biophysics (Eds. W. Hoppe, W. Lohmann, H. Markl, H. Ziegler), Springer Verlag Berlin 1983. By mixing two lipids where one component is electrically neutral and the other is negatively charged, and with at least one component being saturated and exhibiting a phase transition temperature $T_c$ in a range that is acceptable for proteins (e.g. 0° C.–8° C.), one can prepare temperature dependent surface charge patterns of the bilayer coating as reported by E. Sackmann in "Charge induced changes of the microstructure of membranes" on p. 438 in Biophysics (Eds. W. Hoppe, W. Lohmann, H. Markl, H. Ziegler), Springer Verlag Berlin 1983. A quasi-two dimensional domain formation (domain size in the nm–µm range) can take place under suitable conditions in the crystalline phase ($T<T_c$), where the domains contain different proportions of the electrically charged lipid. Thus, crystalline domains with high negative surface charge density can float in a fluid matrix with low negative surface charge density. FIG. 2 shows schematically that positively charged proteins will then couple to the crystalline domains with high affinity via Coulomb interaction. Raising the temperature to a level above the phase transition temperature ($T>T_c$) will cause the domains to disappear due to melting of the crystalline regions and the homogeneous distribution of the electrically charged component over the bilayer by means of lateral diffusion. This situation is decpicted schematically in FIG. 3. As a result, the coupling strength between protein and bilayer surface undergoes a drastic decrease and the previously coupled protein can detach from the surface (cf. example 3, below).

In the following three examples of the procedure will be discussed.

EXAMPLE 1

Gel filtration of proteins with different molecular weight.

A standard chromatography column is packed with a commercially available silica gel (i.e. porous spheres of silicon dioxide of 3 µm diameter and a pore size of 100 nm) and then the column is filled with buffer medium of a pH in the range 3–9 (depending on the particular elution conditions).

Coating of the silica gel

Natural phosphatidylcholine (lecithin) is used as the coating lipid. The lyophilized lipid powder is dissolved in 10 ml buffer medium at room temperature and incubated for 15 min. under gentle vortexing. After this, the dispersion is sonicated with a rod ultrasonicator at high power for 10–15 min. until the previously milky dispersion appears to be optically clear. The amount of lipid used in the preparation is calculated in such a way, that it roughly corresponds to that amount required to coat the surface of the gel (including the pores) with a bilayer, assuming 80 Å$^2$ as the surface area per lecithin molecule. The small unilamellar vesicles with diameters in the range 40–100 nm obtained by the sonication are then added to the column and eluted. The vesicles collapse upon the contact with the silica surface and a closed and stable lipid bilayer is formed on it. Excess vesicles are removed by the elution. After flushing the column with buffer medium it is ready for the gel filtration.

An alternative way is to achieve the coating outside the column, i.e. prior to packing. This is done by vortexing the lecithin vesicles solution and the silica spheres (silica gel) in buffer for approx. 1 minute. Then the coated gel is washed five times using a table top centrifuge (i.e. dispersion of the coated gel in an excess volume of buffer, centrifugation and removal of the supernatant that may contain excess vesicles) and after this is ready to be packed into the column.

Gel filtration

The protein mixture to be separated (dissolved in buffer medium) is added to the column. On their way through the column the small proteins of the mixture get retarded by interaction with the pores. The lecithin bilayer coating now prevents the possible denaturation of these proteins. The protein fractions are collected according to their molecular weight using a fraction collector at the exit of the column.

EXAMPLE 2

Ion exchange chromatography of a protein mixture having differently charged components Preparation of the column The preparation of the column is analogous to example 1 with the exception that now a binary lipid mixture of lecithin and phosphatidylserine with a molar ratio of 4:1 is being used. This results in a negative surface charge of the coated bilayer since phosphatidylserine carries a negative excess charge at neutral pH. Moreover, as phosphatidylserine prefers bilayer regions of high curvature it will get enriched in the pores of the coated silica gel and thus create there a high negative surface potential. An alternative column preparation method can be applied when a column packed with a pure lecithin coated silica gel is already available. Then small unilamellar vesicles of phosphatidylserine (prepared as described above) are added to the column and eluted. On their way through the column the vesicles exchange phosphatidylserine with the lipids of the bilayer coated to the silica gel (lecithin). Thus, the coating aquires a negative surface charge. The column is ready for the chromatography run after flushing it with buffer in order to remove the remaining vesicles.

If desired, a positively charged surface of the bilyer can be obtained by substituting the negatively charged lipid in the preparation procedure by a lipid-like amphiphile that carries a positive excess charge, e.g. DODAB (dimethyldioctadecyl ammonium bromide).

Chromatography run

The protein mixture to be separated is added to the column and eluted under neutral pH and at low ionic strength of the buffer medium. Proteins with an electrically positive excess charge get coupled to the gel surface or inside the pores via Coulomb interactions while negatively charged or neutral proteins pass the column accelerated or unaffected, respectively. The lipid bilayer prevents the possible denaturation of the coupled proteins. After the elution of the negatively charged and neutral protein components of the mixture, a buffer of high ionic strength (e.g. with 200 mM NaCl) is introduced to the column. Alternatively, detergent solutions of low concentration can be used. The ions detach the electrostatically bound proteins from the surface so that the latter can be collected with the fraction collector at column exit. Hence, positively charged proteins are separated out of the mixture while preventing their denaturation and thus enabling a high yield of protein activity.

EXAMPLE 3

Charge selective elution of proteins by temperature induced changes of the protein coupling characteristics of the column Column preparation Silica beads without pores are used for packing the column. Alternatively silica gels (i.e. porous silica spheres) can be used. They are coated with a lipid bilayer according to procedures described above. A binary lipid mixture of 1-palmitoyl-2-oleoyl-sn-glycero-3-phosphocholine (POPC) containing 20 mol % 1,2-dimyristoyl-sn-glycero-3-phosphatidylglycerol (DMPG) is used for the coating. This mixture exhibits a phase transition temperature $T_c$ of approximately 4° C.

Chromatography run

A protein mixture containing proteins with different excess charges is introduced to the column at a temperature of 1° C. At this temperature, the lipid bilayer exhibits crystalline domains containing a high proportion of the negatively charged DMPG.

Positively charged proteins (and among them most preferentially those with the highest excess charge) couple to the lipid bilayer on their way through the column. After the elution of the negatively charged and of the neutral proteins the column temperature is increased to 8° C., so that the bound proteins get detached from the surface due to the dissolution of the crystalline domains and can be eluted.

What is claimed is:

1. A process for separating proteins according to their molecular weight or their electrical charge state while protecting the proteins against denaturation comprising:

coating a silica or silicon-based solid substrate with a lipid layer, contacting a sample containing proteins with the lipid layer coated silica or silicon-based solid substrate, and eluting at least some of the proteins from the lipid layer coated silica or silicon-based solid substrate, wherein individual proteins are separated based upon their interaction with the lipid layer coated solid silica or silicon-based substrate.

2. A process according to claim 1, wherein said silica or silicon-based solid substrate is chromatography packing material.

3. A process according to claim 1, wherein said eluting at least some of the proteins is performed by raising the temperature.

4. In a chromatography process for separating proteins according to their molecular weight or their electrical charge state while protecting the proteins against denaturation comprising contacting a sample containing proteins with a silica or silicon-based solid substrate, and eluting the proteins from the silica or silicon-based solid substrate, wherein individual proteins are separated based upon their interaction with the silica or silicon-based solid substrate, the improvement comprising coating the silica or silicon-based solid substrate with a lipid bilayer before contacting a sample containing proteins with the coated silica or silicon-based solid substrate.

5. A process according to claim 4, wherein said lipid bilayer is coated on the solid substrate by absorption and fusion of unilamellar vesicules onto a surface of the solid substrate.

6. A process according to claim 4, wherein said lipid bilayer comprises phospholipids.

7. A process according to claim 6, wherein said phospholipids are phosphatidylcholines.

8. A process according to claim 4, wherein said lipid bilayer has modified surface charge properties by having phospholipids carrying a negatively charged group or amphiphiles with a positively charged group.

9. A process according to claim 4, wherein said lipid bilayer consists of at least two components and the mixing behavior of the two components creates an electrical charge pattern on the lipid layer surface.

10. A process according to claim 4, wherein said lipid bilayer promotes specific binding or coupling of proteins to the lipid layer surface.

11. A process according to claim 4, wherein said solid substrate is silica gel or other porous silica.

12. A process according to claim 4, wherein said solid substrate contains a polymer suitable for chromatography packing material.

13. A process according to claim 4, wherein lipids in said lipid bilayer are amphiphiles or mixtures containing amphiphiles which form a lipid layer.

14. A process according to claim 4, wherein said solid substrate is chromatography packing material for column chromatography or high performance liquid chromatography.

15. A process according to claim 4, wherein said solid substrate is chromatography packing material for gel chromatography of proteins wherein the proteins are separated according to their individual molecular weight.

16. A process according to claim 4, wherein said solid substrate is chromatography packing material for charge selective chromatography of proteins where the proteins are separated according to their electrical charge.

17. A process according to claim 4, wherein said eluting the proteins is performed by raising the temperature.

* * * * *